United States Patent [19]

Sipos

[11] Patent Number: 4,664,906

[45] Date of Patent: May 12, 1987

[54] ORAL COMPOSITIONS

[75] Inventor: Tibor Sipos, Lebanon, N.J.

[73] Assignee: Johnson & Johnson Products Inc., New Brunswick, N.J.

[21] Appl. No.: 645,634

[22] Filed: Aug. 30, 1984

[51] Int. Cl.[4] .......................... A61K 7/16; A61K 33/30
[52] U.S. Cl. ................................. 424/49; 424/145; 514/902
[58] Field of Search .................... 424/49, 145; 514/902

[56] References Cited

U.S. PATENT DOCUMENTS

| | | | |
|---|---|---|---|
| 2,393,826 | 1/1946 | Senkus | 260/309 |
| 3,357,886 | 12/1967 | McMillan | 424/49 |
| 3,888,976 | 6/1975 | Mlkvy et al. | 424/44 |
| 4,022,880 | 5/1977 | Vinson et al. | 424/49 |
| 4,146,607 | 3/1979 | Ritchey | 424/145 |
| 4,160,821 | 7/1979 | Sipos | 424/145 |
| 4,395,398 | 7/1983 | Yamamoto | 424/145 |
| 4,406,881 | 9/1983 | Ladanyi | 424/145 |

FOREIGN PATENT DOCUMENTS 4501M 10/1966 France .

OTHER PUBLICATIONS

J. Am. Pharm. Assoc. 32(2) 33–44 (1943)–Sprowls et al.

Primary Examiner—Douglas W. Robinson
Attorney, Agent, or Firm—Steven P. Berman

[57]  ABSTRACT

Oral compositions which exhibit antimicrobial activity containing hexedine and a pharmaceutically acceptable zinc compound.

8 Claims, No Drawings

ORAL COMPOSITIONS

BACKGROUND OF THE INVENTION

This invention relates to "oral compositions" which term is used herein to designate products which, in the ordinary course of usage, are retained in the oral cavity for a time sufficient to contact substantially all of the dental surfaces but are not intentionally ingested. Such products include, for example, dentifrices, mouthwashes, chewing gums, prophylaxis pastes, non-abrasive gels, topical solutions and the like. This invention more specifically relates to oral compositions which exhibit antimicrobial properties which help to retard the accumulation of dental plaque and/or calculus on the teeth and gums.

Dental plaque is a complex organic film which adheres to and coats the oral hard andd soft tissues. The formation and properties of dental plaque are extremely important in the maintenance of oral health since plaque harbors the bacteria which produce dental caries, gingivitis and periodontitis. In fact, dental plaque is composed essentially of bacterial colonies growing in an interbacterial organic matrix that provides adherence of the colonies to the teeth and gingiva and coherence of the colonies to one another. Thus, the elimination or inhibition of dental plaque is related to and beneficial in reducing the incidence of dental caries, gingival inflammation and periodontitis.

As is well known to those skilled in the art, dental caries is caused principally by dissolution of tooth mineral by biologically produced intra-oral acids. Such biologically produced intra-oral acids primarily are produced by some of the bacterial colonies that constitute dental plaque. Gingival inflammation, which is the first stage of the more severe periodontitis, is produced by the inflammatory products of bacterial plaque metabolism. Among these bacterial metabolites one can mention hydrolytic enzymes, endotoxins and antigens. Thus, the elimination of the medium which comprises such caries and gingivitis producing bacteria is believed to directly affect the incidence of dental caries and periodontitis.

The formation of dental plaque is not fully understood but it is known to result from the growth and colonization of various species of oral bacteria on the surface of the teeth and gingiva. Further, there is believed to be a direct relationship between the ability of dental plaque to induce the precipitation (crystallization) of calcium salts on the surface of the teeth and formation of dental calculus.

Dental calculus is a hard deposit found on the surfaces of the teeth which results from the precipitation of calcium salts in an organic matrix, primarily plaque. Thus, calculus can be defined as calcified plaque. The elimination and retardation of the formation of dental plaque is an important factor in dental hygienic and health programs not only in the reduction of dental caries and periodontal disease but also the reduction of the formation of dental calculus.

The utilization of antibacterial or antimicrobial agents such as antiseptics and germicides for topical application in the oral cavity is well known in the art. By way of explanation, an antiseptic ordinarily is considered to be an agent which stops or inhibits the growth of microorganisms without necessarily killing them. In contrast, a bacteriocide or germicide is any substance which kills or destroys bacteria. Frequently, the difference between bacteriostatic and bacteriocidal effects is a quantitive function of the concentration of the antibacterial agents.

Less irritating antiseptics find wide usage for topical application on the oral mucosa for the control of minor infections and on dried mucosa in preparation for needle insertion. Antiseptics too irritating for use on soft tissue find application within the tooth structure for root canal sterilization or cavity medication. Germicides have also been incorporated in commercial mouthwashes which are medicated liquids used for cleaning the mouth or treating disease states in the oral mucous membrane.

The use of such antiseptic agents has many times resulted in severe staining problems with the teeth which would mitigate against their use even if they were effective against plaque.

SUMMARY OF THE INVENTION

It is an object of this invention to provide improved oral compositions.

It is another object of this invention to provide improved oral compositions which exhibit antimicrobial properties to aid in the prevention of plaque, calculus, gingival diseases and caries formation.

It is a further object of this invention to provide improved antimicrobial oral compositions which do not present significant tooth staining or other problems.

Other objects of this invention will be set forth in, or be apparent from, the following detailed description of the invention.

The foregoing objects and other features and advantages of the present invention are achieved by oral compositions comprising a synergistic combination of a specific antimicrobial agent and a pharmaceutically acceptable zinc compound.

DETAILED DESCRIPTION OF THE INVENTION

This invention relates to oral compositions comprising a synergistic combination of hexedine and a pharmaceutically acceptable zinc compound. The term "synergistic combination" as used herein refers to a mixture of two discrete compounds which display a degree of total antimicrobial activity which is greater than the average of the sum of antimicrobial activity of the compounds taken individually.

Hexedine or 2,6-Bis(2-ethylhexyl)hexahydro-7α-methyl-1H-imidazo[1,5-c]imidazole is a compound of the formula

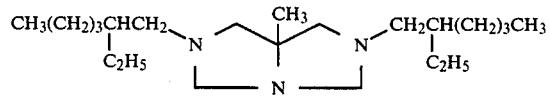

This compound was disclosed in U.S. Pat. Nos. 2,393,826 and 3,357,886 and a process for its preparation is disclosed in U.S. Pat: No. 3,395,154. This process involves treating at about equimolar ratio 5-amino-1,3-bis[2-ethylhexyl]5-methylhexahydropyrimide of the formula

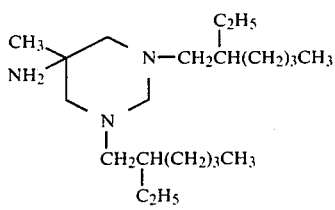

which is available commercially as hexetidine with an aqueous solution of formaldehyde. The reaction may be effected at reflux temperature with or without the use of a solvent and results in the formation of hexedine. The teachings of these references are incorporated herein by reference.

The zinc salts that are suitable for use in the compositions of this invention include zinc chloride, zinc sulfate, zinc citrate, zinc acetate, zinc lactate, zinc salicylate, zinc thiocyanate, zinc gluconoheptanoate, zinc gluconate, zinc maleate, zinc fumarate and, more generally, any pharmaceutically acceptable zinc salt.

The ratio of compounds in the synergistic combination of this invention can vary from about 1:1 to 1:32, preferably 1:4, hexedine to zinc compound.

Consistent with the above ratios, the zinc ion should be present in an effective amount, while the hexedine concentration should be from as low as 0.0025% up to about 2% by weight. The preferred range of hexedine concentration is about 0.05% to about 1.0% by weight, more preferably about 0.05 to about 0.2%. Similarly, the zinc ion concentration should be from about 0.01 to about 25.0% by weight, preferably about 0.05 to 4.0% by weight. While higher concentrations of both zinc and hexedine could be used, no particular advantage would be gained.

The foregoing synergistic combination of hexedine and zinc compound is preferably applied to the oral hard and soft tissues by means of a carrier suitable for use in the oral cavity. Suitable carriers include dentifrices, prophylaxis pastes, mouthwashes, non-abrasive gels, chewing gums, topical solutions, and the like. When used in such compositions, the synergistic compositions are present in about 0.2% to about 3.0% by weight of the total compositions, In the case of topical solutions and mouthwashes, suitable carriers include water and other liquids. Other carriers include various compatible plastics, e.g., nylon, polyethylene, polypropylene and the like, and other materials, e.g., natural bristles, wood, and the like, which may be formed into toothbrushes or interdental stimulators and thus utilized to apply the active agents of the present invention to the oral hard and soft tissues. Also, other carriers include waxes, plastics, or any other binders or sizings used on dental flosses and tapes or chewing gum which contact the oral hard and soft tissues during use or consumption. Indeed, substantially any device or implement capable of supplying the active agents to the oral hard and soft tissues may serve as a suitable carrier in accordance with this invention.

A preferred embodiment of the present invention includes the synergistic combinations of the present invention plus the addition of a pharmaceutically acceptable fluoride compound. Typical pharmaceutically acceptable fluoride compounds suitable for use include sodium fluoride, potassium fluoride, lithium fluoride, aluminum fluoride, zinc fluoride, stannous fluoride, sodium monofluorophosphate, acidulated phosphate fluoride, ammonium fluoride, ammonium bifluoride and amine fluoride.

Suitable pharmaceutically acceptable oral hygiene vehicles that may be used alone or in combination in the compositions of the present invention include glycerol, water, ethanol, polyethylene glycol, propylene glycol, sorbitol and the like. Other vehicles may be used if compatible with the other ingredients in the compositions.

If the compositions of the present invention are in the form of a dentifrice, they should also contain a suitable abrasive. The abrasive should be such that it does not harm the enamel or dentin while being capable of cleaning and polishing the teeth as well as being compatible with the synergistic combinations of the present invention. Preferred abrasives include the silica abrasives such as the hydrated silicas and silica gels and comprise from about 5.0 to 97.0% by weight of the dentifrice compositions.

Dentifrices require a binder substance to impart desired textural properties. Natural gum binders such as gum tragacanth, gum karaya and gum arabic and seaweed derivatives such as Irish moss and alginates, and water soluble cellulose derivatives, such as hydroxyethyl cellulose and sodium carboxymethyl cellulose, can be used for this purpose. Desirably, those materials are employed which are most compatible with the synergistic compounds. Binders which have no ionic groups, such as hydroxyethyl cellulose, are especially preferred; however, selected ionic binders can occasionally be used. Improvements in texture can also be attained by including an additional material such as colloidal magnesium aluminum silicate. Thickening agents in an amount of from 0.5 to 5.0% by weight can also be used to form a satisfactory dentifrice.

Another component in dentifrice compositions is a humectant. The humectant serves to keep the dentifrice compositions from hardening upon exposure to air and also imparts a desirable sweetness to the formulations to minimize the astringency ascribed to the zinc chloride. The humectant, on a pure humectant basis, generally comprises from about 1.0 to 80.0%, preferably from about 8.0 to 50.0% by weight of the total compositions. Suitable humectants include edible polyhydric alcohols such as glycerol, sorbitol, xylitol and propylene glycol. Mixtures of glycerol and sorbitol are especially preferred.

Water is another essential component of dentifrice compositions. Water employed in the preparation of commercially suitable dentifrices should preferably be deionized and free of impurities. Water comprises from about 0.05 to 70.0%, preferably from about 15.0 to 50.0% by weight of the formulations. These amounts of water include the free water which is added plus that which is introduced with other materials.

Another ingredient of dentifrice compositions is a suitable surface-active agent or detergent. Suitable surface-active agents are those that are reasonably stable, foam through the pH range and are compatible with the synergistic compounds as well as the other components. These agents are usually water-soluble, organic compounds and may be anionic, nonionic or cationic in nature.

Such materials are well-known and include, for example, the water-soluble salts of high fatty acid monoglyceride monosulfates such as sodium coconut acid monoglyceride monosulfate; higher alkyl sulfates such as sodium lauryl sulfate, alkyl aryl sulfonate such as sodium dodecyl benzene sulfonate, higher fatty acid esters of 1,2-di-hydroxypropane sulfonate, and sodium salts of the coconut fatty acid amide of N-methyltaurine. The latter is particularly preferred since it has been found to minimize the astringency of zinc chloride. Particularly useful are the nonionic block copolymers derived from the condensation of polyethylene glycol and polypropylene glycol. These block copolymers are available from Wyandotte Chemical Corp. under the tradename "Pluronic". These block copolymers are available in liquid, paste or solid form. The preferred nonionic block copolymers are the solid materials such as Pluronic F-85, Pluronic F-108 and Pluronic F-127.

Another preferred nonionic detergent is the cogeneric mixture of conjugated polyoxybutylene-polyoxyethylene described in U.S. Pat. No. 4,323,552 sold under the tradename "Butronic" by BASF Wyandotte Corporation. Butronic Polyol L-1 and Butronic Polyol R-1 are particularly preferred.

The Pluronic and Butronic nonionic surface-active agents have been found to minimize the astringency of the zinc chloride and can be present in the amount of from about 0.5 to 10%, preferably about 1.0 to 5.0%.

Other nonionic surface-active agents which may be employed are the condensates of sorbitan monostearate with approximately 20 moles of ethylene oxide. Amphoteric agents include the quaternized imidazole derivatives which are available under the tradename "Miranol" such as Miranol C2M, from the Miranol Chemical Company. Cationic surface-active agents can also be used. These compounds have detergent properties as well as germicidal and antibacterial properties. Examples of suitable cationic detergents are benzyl ammonium chloride, benzyl dimethyl stearylammonium chloride, tertiary amines having one fatty alkyl group of from 1–18 carbon atoms and two (poly)oxyethylene groups attached to the nitrogen and salts thereof with acids, and compounds of the structure:

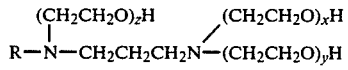

where R is a fatty alkyl group and can have from about 12 to 18 carbon atoms, and x, y, and z total 3 or higher, as well as salts thereof with mineral or organic acids, may also be used. About 0.5% to 15% by weight of these cationic surface-active agents can be used in dentifrice compositions.

In addition to the above described components, the dentifrice can contain a variety of optional conventional dentifrice ingredients. Such optional ingredients include preservatives, flavoring agents, sweetening agents, coloring agents and pigments.

Suitable flavoring agents include oil of wintergreen, oil of peppermint, oil of spearmint, oil of sassafras, and oil of clove. Sweetening agents which can be used include saccharin, dextrose, levulose, aspartame, trichlorogalactosucrose, D-tryptophan, dihydrochalcones and sodium cyclamate. Flavoring agents are generally utilized in dentifrices at levels of from about 0.01% to 2% by weight and sweetening agents at levels of from about 0.05% to about 2% by weight.

These dentifrice compositions are prepared by mixing together the components by conventional means. Once prepared, the compositions have a pH of from about 3.5 to 6.0, when said compositions are slurried with water in a 3:1 weight ratio of water to composition. These dentifrice compositiions are used in conventional manner, i.e., the compositions or slurries are brushed onto dental surfaces and subsequently rinsed away. During use of the dentifrices in this manner, pastes or slurries generally contact dental surfaces for at least about 30 seconds. More preferably, such pastes or slurries contact dental surfaces for at least about 60 seconds.

While the previous discussions have been directed to dentifrice compositions, the present invention may also encompass compositions in the form of a mouthwash, gel, powder, solution, varnish, lozenge, chewing gum, slow release device or other form suitable for oral application. Any pharmaceutically acceptable material, such as those ordinarily used in such oral compositions, that are compatible with the synergistic combinations may be employed.

Specific embodiments of the present invention are illustrated by the following representative examples. It will be understood, however, that the invention is not confined to the specific limitations set forth in the individual examples but rather to the scope of the appended claims.

All percentages used herein are by weight unless otherwise designated.

EXAMPLE I

An opacified dentifrice is prepared by conventional means and has the following formulation:

|  | % w/w |
|---|---|
| zinc chloride | 2.00 |
| hexedine | 0.20 |
| sodium benzoate | 0.20 |
| sodium saccharin | 0.50 |
| glycerin | 10.00 |
| hydroxyethylcellulose | 1.00 |
| xanthan gum | 1.00 |
| hydrated silica | 20.00 |
| Zeothix 265 | 5.00 |
| sorbitol 70% | 12.00 |
| titanium dioxide | 0.50 |
| Poloxamer 237 | 3.00 |
| flavoring | 1.00 |
| deionized water q.s. to | 100.00 |

EXAMPLE II

Another opacified dentifrice having the following composition is formulated:

|  | % w/w |
|---|---|
| hexedine | 0.20 |
| sodium fluoride | 0.22 |
| zinc chloride | 2.00 |
| sorbitol (70% aqueous) | 35.00 |
| glycerin | 10.00 |
| hydrated silica | 23.00 |
| sodium methylcocoyl taurate | 3.75 |
| xanthan gum | 1.00 |
| hydroxyethylcellulose | 1.00 |
| sodium gluconate | 0.80 |
| titanium dioxide | 0.80 |
| sodium saccharin | 0.70 |
| saccharin | 0.10 |
| sodium benzoate | 0.20 |
| flavoring | 1.30 |
| deionized water q.s. to | 100.00 |

EXAMPLE III

Another opacified dentifrice having the following composition is formulated:

| | % w/w |
|---|---|
| hexedine | 0.10 |
| sodium fluoride | 0.22 |
| zinc chloride | 0.50 |
| sorbitol (70% aqueous) | 40.00 |
| glycerin | 15.00 |
| hydrated silica | 23.00 |
| polyethylene glycol | 5.00 |
| sodium methylcocoyl taurate | 3.75 |
| xanthan gum | 0.50 |
| hydroxyethylcellulose | 0.50 |
| sodium saccharin | 0.50 |
| saccharin | 0.30 |
| sodium gluconate | 0.27 |
| sodium benzoate | 0.20 |
| titanium dioxide | 0.20 |
| flavoring | 1.00 |
| deionized water q.s. to | 100.00 |

EXAMPLE IV

A gel dentifrice is prepared according to conventional means containing the following ingredients:

| | % w/w |
|---|---|
| hexedine | 0.20 |
| zinc chloride | 0.50 |
| sorbitol (70% aqueous) | 50.00 |
| glycerin | 5.00 |
| hydrated silica | 23.00 |
| polyethylene glycol | 5.00 |
| sodium methylcocoyl taurate | 3.75 |
| xanthan gum | 0.50 |
| hydroxyethylcellulose | 0.50 |
| sodium gluconate | 0.27 |
| sodium saccharin | 0.50 |
| saccharin | 0.15 |
| sodium benzoate | 0.20 |
| flavoring and coloring | 0.70 |
| deionized water q.s. to | 100.00 |

EXAMPLE V

A tooth powder composition is prepared according to conventional means containing the following ingredients:

| | % w/w |
|---|---|
| silica gel | 96.50 |
| zinc chloride | 0.50 |
| hexedine | 0.20 |
| aspartame | 0.50 |
| sodium methylcocoyl taurate | 1.50 |
| flavoring | 0.80 |

EXAMPLE VI

A mouthrinse composition is prepared according to conventional means containing the following ingredients:

| | % w/w |
|---|---|
| ethyl alcohol (190 proof) | 10.00 |
| Poloxamer 407 | 1.75 |
| zinc chloride | 0.25 |
| hexedine | 0.10 |
| sodium fluoride | 0.05 |
| sodium gluconate | 1.00 |
| sorbitol solution, 70% | 12.50 |
| sodium saccharin | 0.02 |
| flavoring and coloring | 1.50 |
| deionized water q.s. to | 100.00 |

EXAMPLE VII

A lozenge composition is prepared according to conventional means and contains the following ingredients:

| | % w/w |
|---|---|
| sorbitol powder | 74.65 |
| corn syrup | 15.00 |
| zinc chloride | 0.50 |
| hexedine | 0.20 |
| flavoring and coloring | 1.15 |
| sodium gluconate | 0.30 |
| sodium saccharin | 0.20 |
| tableting lubricant | 5.00 |
| deionized water | 3.00 |

EXAMPLE VIII

A quantitative technique was used to determine the synergistic effect of a zinc compound on the ability of hexedine to inhibit the growth of various bacteria. Briefly, serial dilutions of the test compounds were made in microtiter plates containing 32 µg/ml or 128 µg/ml zinc chloride admixed with Schaedler broth. The microtiter wells were then inoculated with a standardized inoculum prepared by resuspending the bacterial colonies from the surface of the agar plates with Schaedler broth and diluting it to a concentration that contained $10^5$ to $10^7$ bacteria per ml. The microtiter plates were incubated at 37° C. under anaerobic conditions for 48 hours and the minimal inhibitory concentrations (MIC's) were recorded as the lowest concentrations of the test compound that inhibited visible bacterial growth. The results are shown below in Table I.

TABLE I

| | MIC/µg/ml | | Hexedine + Zinc Chloride 32 µg/ml | Hexedine + Zinc Chloride 128 µg/ml |
|---|---|---|---|---|
| Bacterium | Hexedine alone | Zinc Chloride alone | | |
| B. melaninogenicus | 8 | 128 | 1 | <1 |
| B. intermedius | 4 | 128 | 4 | <1 |
| B. asaccharolyticus-381 | 8 | 128 | 1 | <1 |
| B. asaccharolyticus-2561 | 8 | 128 | 4 | <1 |
| B. asaccharolyticus-13-12 | 4 | 128 | 4 | <1 |
| V. acalescens | 8 | 128 | 4 | 4 |
| P. virabilis | 8 | 128 | 8 | 1 |
| P. asaccharolyticus | 4 | 128 | 8 | 1 |
| A. odontolyticus | 8 | 128 | 16 | 4 |
| A. viscosus | 8 | 128 | 8 | 2 |
| L. casi | 8 | 128 | 8 | 2 |
| S. salivarius | 16 | 128 | 8 | 1 |
| S. mitis | 8 | 128 | 8 | 1 |
| S. mutans-245 | 8 | 128 | 8 | 1 |
| S. mutans-6715 | 8 | 128 | 4 | <1 |
| S. sanguis | 4 | 128 | 2 | <1 |
| F. nucleatum | 32 | 128 | 8 | <1 |

The results clearly show that the zinc chloride enhances the antimicrobial activity of the hexedine.

EXAMPLE IX

In order to determine the efficacy of the compositions of the present invention, an experiment was conducted relating to gingivitis and plaque accumulation in the beagle dog.

The test was conducted as follows: 24 beagle dogs, age 2-4 years, were utilized and divided into four groups of six dogs each. Each group was treated with a different dentifrice formulation; twice daily for five days, once on the sixth day and not on the seventh day, for a period of fifteen weeks. Formulation A was a placebo containing no zinc chloride or hexedine, formulation B contained 2% zinc chloride and no hexedine, formulation C contained 0.2% hexedine and no zinc chloride and formulation D contained 2% zinc chloride and 0.2% hexedine (Example I). Each of the four quadrants of the mouth of each animal was treated with 500 mg of the dentifrice by rubbing it onto the gingival at the dentogingival junction along the facial surface. Each quadrant was exposed to the formulation for about 15 seconds during each treatment.

At the conclusion of the test, the animals were examined for severity of gingivitis, bleeding and plaque accumulation. It was found that the animals that received formulation D exhibited a reduction in the severity of gingivitis, bleeding, and plaque accumulation. Furthermore, formulation D exhibits overall superiority to the compositions containing zinc chloride (formulation B) or hexedine (formulation C) alone.

Various other features and embodiments of the present invention not specifically set forth herein will be readily obvious to those skilled in the art, all of which may be achieved without departing from the spirit and scope of the invention as defined by the following claims.

What is claimed is:

1. An oral composition comprising a pharmaceutically-acceptable vehicle containing from about 0.0025 to about 2.0% by weight of hexedine and from about 0.01 to about 25.0% by weight of a pharmaceutically-acceptable zinc salt selected from the group consisting of zinc chloride, zinc sulfate, zinc citrate, zinc acetate, zinc lactate, zinc salicylate, zinc thiocyanate, zinc gluconoheptanoate, zinc gluconate, zinc maleate, and zinc fumarate wherein the hexedine and zinc are present in a weight ratio of from about 1:1 to 1:32.

2. The composition of claim 1 wherein hexedine is present in a concentration of from about 0.05 to about 1.0% by weight.

3. The composition of claim 1 wherein hexedine is present in a concentration of from about 0.05 to about 0.2% by weight.

4. The composition of claim 1 wherein the zinc ion is present in a concentration of from about 0.05 to 4.0% by weight.

5. The composition of claim 1 wherein said vehicle comprises at least one member selected from the group consisting of glycerol, water, ethanol, polyethylene glycol, propylene glycol and sorbitol.

6. A method of preventing or reducing the incidence of gingivitis comprising applying to the teeth and gingavae of the subject to be treated a therapeutically effective amount of the composition of claim 1.

7. The method of claim 6 wherein said composition is applied at least once daily.

8. The method of claim 6 wherein said composition is applied twice daily.

* * * * *